United States Patent [19]

Wetter et al.

[11] Patent Number: 4,556,717
[45] Date of Patent: Dec. 3, 1985

[54] PROCESS FOR PRODUCING 1-[2-(2,4-DICHLOROPHENYL)-PENTYL]-1H-1,2,4-TRIAZOLE

[75] Inventors: Hansjürg Wetter, Therwil; Peter Baumeister, Flüh; Paul Radimerski, Arisdorf; Pierre Martin, Rheinfelden, all of Switzerland

[73] Assignee: Ciba Geigy Corporation, Ardsley, N.Y.

[21] Appl. No.: 505,019

[22] Filed: Jun. 16, 1983

[30] Foreign Application Priority Data

Jun. 18, 1982 [CH] Switzerland .......................... 3773/82

[51] Int. Cl.$^4$ ........................................... C07D 249/08
[52] U.S. Cl. ....................................... 548/262; 560/34; 564/34; 564/36; 564/149; 564/151; 564/251; 564/313
[58] Field of Search .......................... 548/262; 564/313

[56] References Cited

U.S. PATENT DOCUMENTS

| | | | |
|---|---|---|---|
| 2,885,399 | 5/1959 | Omietanski | 564/313 |
| 2,909,567 | 10/1959 | Rudner | 564/313 |
| 3,197,474 | 7/1965 | Biel | 564/313 |
| 3,197,501 | 7/1965 | Biel | 564/313 |
| 3,213,138 | 10/1965 | Biel | 564/313 |
| 3,359,316 | 12/1967 | Biel | 564/313 |

FOREIGN PATENT DOCUMENTS

2735872  2/1978  Fed. Rep. of Germany ....... 548/262

OTHER PUBLICATIONS

Elderfield, Heterocyclic Compounds, vol. 7, (New York, 1961), pp. 433–434, 440–441.
Pleininger et al., Chem. Ber., 88, 1956 (1955).

Primary Examiner—Alton D. Rollins
Attorney, Agent, or Firm—Karl F. Jorda

[57] ABSTRACT

1-[2-(2,4-Dichlorophenyl)-pentyl]-1H-1,2,4-triazole can be produced, in a novel, simple, economical and isomer-free form, by reacting 2-(2,4-dichlorophenyl)-valeronitrile, in the presence of hydrogen, an acid and a hydrogenation catalyst, with a compound H$_2$N—NH—R to a compound of the formula

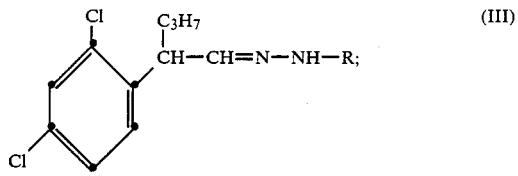

hydrogenating the compound (III) catalytically to a compound

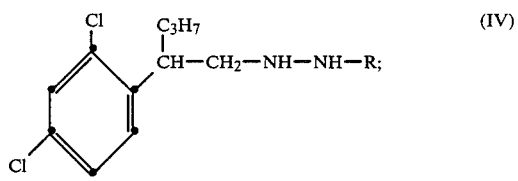

hydrolysing compounds (IV) wherein R is not hydrogen, and converting the compounds (IV) wherein R=H, or salts thereof, with formamide and/or [3-(dimethylamino)-2-azaprop-2-en-1-ylidene]-dimethylammonium chloride, into 1-[2-(2,4-dichlorophenyl)-pentyl]-1H-1,2,4-triazole, or converting compounds (IV) wherein R=—COR', with aqueous formic acid, into the corresponding N,N'-bisformyl derivatives, and reacting these with formamide, optionally in the presence of NH$_3$, to 1-[2-(2,4-dichlorophenyl)-pentyl]-1H-1,2,4-triazole. R in the formulae is hydrogen, —CHO, —COR', —COOR' or —CONH$_2$, and R' is C$_1$–C$_4$-alkyl, benzyl or phenyl.

1-[2-(2,4-Dichlorophenyl)-pentyl]-1H-1,2,4-triazole exhibits fungicidal activity, and can be used to control phytopathogenic fungi.

9 Claims, No Drawings

PROCESS FOR PRODUCING 1-[2-(2,4-DICHLOROPHENYL)-PENTYL]-1H-1,2,4-TRIAZOLE

The present invention relates to a novel process for producing 1-[2-(2,4-dichlorophenyl)-pentyl]-1H-1,2,4-triazole, and also to novel hydrazone or hydrazine derivatives developed for the production of this compound.

It is known from the German Offenlegungsschrift No. 2,735,872 that fungicidal 1-(2-arylethyl)-1H-1,2,4-triazoles, inter alia 1-[2-(2,4-dichlorophenyl)-pentyl]-1H-1,2,4-triazole, can be obtained by reaction of 1H-1,2,4-triazole, or of an alkali metal salt thereof, with a reactive ester of suitable 2-arylethyl derivatives X—CH$_2$CH(Ar)(R) (Ar=unsubstituted or substituted aryl, R=inter alia alkyl, X=for example —OSO$_2$CH$_3$). Isomeric mixtures of 1H-1,2,4- and 1H-1,3,4-triazole derivatives are formed, of which only the former exhibit fungicidal activity. These isomeric mixtures can be separated only at very high cost. The stated reactive esters for their part have to be produced by means of a multistage synthesis, which involves converting corresponding arylacetonitriles NC—CH(Ar)(R), in the presence of a strong non-oxidising acid, such as HCl, into esters R'OOC—CH(Ar)(R). These are subsequently reduced, in the presence of an alkali metal hydride, such as lithium aluminium hydride or lithium borohydride, to alcohols HOCH$_2$CH(Ar)(R). These alcohols are finally converted, by treatment with for example methanesulfonyl chloride, into the stated reactive esters. As already mentioned, considerable proportions of inactive 1H-1,3,4-triazole derivatives are formed in this prior known process.

It is necessary for the production of the alcohols to use relatively large amounts of the alkali metal hydrides, which are available only to a limited extent for large-scale commercial applications. The use of such hydrides is moreover undesirable on grounds of safety (fire and explosion danger). The esters R'OOC—CH(Ar)(R) either cannot be reduced catalytically or can be reduced only in very unsatisfactory yields. This prior known process has achieved no commercial importance for the stated reasons.

It was therefore the object of the present invention to provide a novel process applicable also on a large commercial scale, with which process the disadvantages mentioned above could be avoided, and with which 1-[2-(2,4-dichlorophenyl)-pentyl]-1H-1,2,4-triazole could be produced in good to very good yields and, in particular, in an isomer-free form.

According to the novel process of the present invention, 1-[2-(2,4-dichlorophenyl)-pentyl]-1H-1,2,4-triazole of the formula I

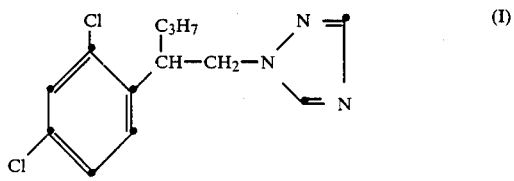

can be produced, in a simple, economical and isomer-free form, by reacting 2-(2,4-dichlorophenyl)-valeronitrile, in the presence of hydrogen, an acid and a hydrogenation catalyst, with a compound of the formula II $$H_2N—NH—R \quad (II)$$

to give a compound of the formula III

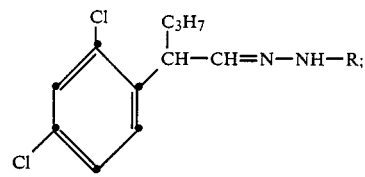

hydrogenating the compound of the formula III catalytically to a compound of the formula IV

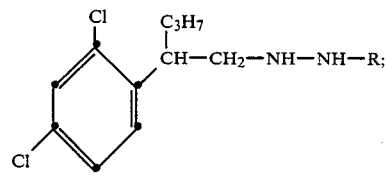

and subsequently either (a) hydrolysing a compound of the formula IV wherein R is not hydrogen, and converting the compound of the formula IV wherein R=H, or a salt thereof with an inorganic or organic acid, with formamide, and/or with [3-(dimethylamino)-2-azaprop-2-en-1-ylidene]-dimethylammonium chloride (Azasalz): ([(CH$_3$)$_2$N$^+$=CH—N=CH—N(CH$_3$)$_2$]Cl$^-$), into a compound of the formula I, or (b) converting a compound of the formula IV wherein R is —COR', with aqueous formic acid, into an N,N'-bisformyl derivative, and reacting this with formamide, optionally in the presence of NH$_3$ or of a substance releasing NH$_3$, into a compound of the formula I; where R is hydrogen, —CHO, —COR', —COOR' or —CONH$_2$, and R' is C$_1$-C$_4$-alkyl, benzyl or phenyl.

Alkyl groups R' can be straight-chain or branched-chain, preferably however straight-chain. Examples which may be mentioned are: methyl, ethyl, n-propyl, isopropyl, n-butyl, sec-butyl and tert-butyl. R is preferably —CHO, —COR' or —COOR', wherein R' is methyl or ethyl. Particularly preferably, R is a group —COR", wherein R" is hydrogen, methyl or ethyl.

The starting products of the formula II and the 2-(2,4-dichlorophenyl)-valeronitrile are known, and can be produced by methods known per se, the last-mentioned for example by alkylation of 2,4-dichlorophenylacetonitrile using customary methods.

The reaction of 2-(2,4-dichlorophenyl)-valeronitrile with the hydrazine of the formula II is advantageously performed in an organic or aqueous-organic medium. Suitable organic solvents are for example: alkanols having up to 6 C atoms, such as methanol, ethanol, n-propanol, isopropanol, butanols and pentanols; and aliphatic and cyclic ethers, such as diethyl ether, di-n-propyl ether, diisopropyl ether, tetrahydropyrane, tetrahydrofuran and dioxane; aromatic and aliphatic hydrocarbons, such as benzene, toluene, xylenes, n-hexane and n-heptane; cyclic or aliphatic amides, such as N-methyl-2-pyrrolidone and N-acetyl-2-pyrrolidone; formamide, and N,N-dialkylamides of aliphatic monocarboxylic acids having 1-3 C atoms in the acid moiety, such as N,N-dimethylformamide, N,N-dimethylacetamide and N,N-diethylacetamide; and/or mixtures of the stated solvents with water. The reaction is preferably performed in a $C_1$-$C_4$-alkanol, especially methanol or ethanol, or in mixtures thereof with water. The reaction temperature for this reaction is not critical: a preferred reaction temperature is between 0° and 150° C., particularly between 20° and 60° C. The reaction can be carried out at normal pressure, or under pressure, preferably between normal pressure and a pressure of up to 10 bar, in particular up to 4 bar.

Types of catalysts known per se can be used as the hydrogenation catalysts. Especially preferred are cobalt, nickel and noble metal catalysts, such as rhodium, platinum, palladium and ruthenium catalysts. Used particularly preferably is Raney nickel or rhodium on a carrier, such as active charcoal or aluminium oxide.

Suitable acids are both inorganic and organic acids, especially inorganic and organic protonic acids. Examples of inorganic protonic acids are hydrohalic acids, such as HCl, HBr and HF, phosphoric acid and sulfuric acid. Suitable organic protonic acid are for example: sulfinic acids, such as benzenesulfinic acid; aliphatic and unsubstituted or substituted aromatic sulfonic acids, such as methanesulfonic acid, benzenesulfonic acid, p-toluenesulfonic acid, naphthalenesulfonic acid, naphthalenedisulfonic acids; aliphatic monocarboxylic acids having preferably 1–18 C atoms, such as formic acid, acetic acid, propionic acid, butyric acid, lauric acid, palmitic acid and stearic acid; halogen-containing aliphatic monocarboxylic acids, such as chloroacetic acid, dichloroacetic acid, trichloroacetic acid and trifluoroacetic acid; aliphatic dicarboxylic acids preferably having 2–12 C atoms, such as oxalic acid, malonic acid, succinic acid, adipic acid and sebacic acid; unsubstituted or substituted aromatic mono- and dicarboxylic acids, such as benzoic acid, toluic acid, naphthoic acid, phthalic acid and terephthalic acid. Weak acids are preferred, such as aliphatic monocarboxylic acids having 1–4 C atoms, such as formic acid, acetic acid, propionic acid and butyric acid. Acetic acid is particularly preferred.

The hydrazine of the formula II and the acid are used advantageously in at least an equimolecular amount; the hydrazine preferably in an equimolecular to double equimolecular amount, and the acid in an equimolecular to fourfold equimolecular amount. Excess acid can under certain circumstances also serve as solvent.

The reaction is preferably performed in the presence of molecular hydrogen. Instead of using molecular hydrogen, it is however also possible under the reaction conditions to use substances releasing hydrogen, such as excess hydrazine, or hypophosphorous acid or salts thereof.

The inventive reaction of 2-(2,4-dichlorophenyl)-valeronitrile with a hydrazine of the formula II yields a hydrazone having readily detachable protective groups. This is surprising since hitherto the conversion of nitrile groups into hydrazones having readily detachable groups has not been possible. It is thus mentioned for example in Chem. Ber., 88, 1956 (1955) that this method yielded no useful results.

The hydrogenation of a hydrazone of the formula III to give a hydrazine of the formula IV is performed advantageously in the presence of an organic solvent. Suitable as such are for example: alkanols, ethers, amides and aromatic or aliphatic hydrocarbons of the aforementioned type, and also aliphatic monocarboxylic acids having 1–5 C atoms, and alkyl esters of aliphatic monocarboxylic acids having a total of 2–6 C atoms, such as formic acid, acetic acid, propionic acid, butyric acid, isobutyric acid, iso- and n-valeric acid; formic acid methyl and -ethyl esters, acetic acid methyl, -ethyl, -n-butyl and -isobutyl esters; esters of carbonic acid, such as dimethyl carbamate and diethyl carbamate, and mixtures of the stated solvents. Particularly preferred are: acetic acid, and alkanols, such as methanol, ethanol, isopropanol, sec-butanol and tert-butanol, and mixtures of these alcohols with ethyl acetate. It is also possible to use mixtures of non-oxidising mineral acids with the solvents mentioned.

The catalysts used for hydrogenation can be those of the types given above, particularly nickel, rhodium, ruthenium and platinum catalysts, more especially however Raney nickel or rhodium and platinum catalysts, optionally on carriers, such as on active charcoal or aluminium oxide. The reaction is advantageously performed at a hydrogen pressure of 1 to 200 bar, particularly 4–100 bar, and at a temperature of between 20° and 120° C., especially between 40° and 100° C.

Before the ring closure reaction, hydrazines of the formula IV wherein R is not hydrogen are hydrolysed, in a manner known per se, in the presence of acids or bases to obtain compounds of the formula IV wherein R=H or salts thereof. The bases used can be for example hydroxides or carbonates of alkali metals or alkaline-earth metals, such as hydroxides or carbonates of sodium, potassium and calcium. The hydrolysis is preferably performed in the presence of a strong acid, especially an inorganic acid, such as HCl, sulfuric acid or phosphoric acid. Hydrolysis can be carried out in an aqueous or aqueous-organic medium, such as in a water/alkanol mixture, particularly in a mixture of water and methanol or ethanol.

For the ring closure reaction according to process variant (a), the formamide and/or the [3-(dimethylamino)-2-azaprop-2-en-1-ylidene]-dimethylammonium chloride is advantageously used in at least an equimolecular amount, relative to the compound of the formula IV (R=H). The reaction is performed with advantage in the presence of an inert organic solvent, for example: alkanols, esters, ethers or amides of the aforementioned type, alkyl nitriles having 2–5 C atoms, such as acetonitrile, propionitrile or butyronitrile; benzonitrile; 3-alkoxypropionitriles having 1 or 2 C atoms in the alkoxy moiety, such as 3-methoxypropionitrile and 3-ethoxypropionitrile. Preferred solvents for the reaction with the 'Azasalz' are $C_1$-$C_5$-alkanols, particularly ethanol. In the reaction with formamide, excess formamide is preferably used as solvent. The reaction temperature for the ring closure reaction according to (a) is in general between 20° and 200° C., preferably between 20° and 180° C.

For the formylation of compounds of the formula IV wherein R is —COR′, for example —COCH$_3$, —COC$_2$H$_5$ or —COC$_3$H$_7$, according to process variant (b), there is preferably used 85% aqueous formic acid; and the reaction temperature is preferably between 70° and 100° C. For the ring closure of the N,N′-bisformyl derivative, the formamide is preferably used in at least an equimolecular amount, relative to the compound of the formula IV (R=—COR′). Suitable substances releasing NH$_3$ are in particular salts of ammonia with weak acids, for example carboxylic acids. Preferred salts are ammonium carbonate, ammonium bicarbonate or ammonium formate. The reaction temperature for the ring closure of the N,N'-bisformyl derivative is in general between 50° and 200° C., preferably between 120° and 180° C.

The 1-[2-(2,4-dichlorophenyl)-pentyl]-1H-1,2,4-triazole of the formula I can be produced according to the present invention in a particularly advantageous manner by reacting 2-(2,4-dichlorophenyl)-valeronitrile, in the presence of acetic acid and a hydrogenation catalyst, with an acylhydrazine of the formula IIa

to a 1-[2-(2,4-dichlorophenyl)-pentylidene]-2-acylhydrazine of the formula IIIa

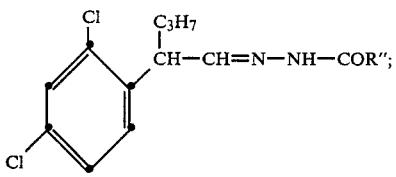

hydrogenating this to 1-[2-(2,4-dichlorophenyl)-pentyl]-2-acylhydrazine of the formula IVa

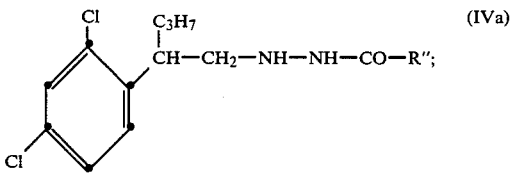

and converting this, by reaction with formic acid, firstly into 1-[2-(2,4-dichlorophenyl)-pentyl]-1,2-diformylhydrazine, and this, by further reaction with formamide at 120°–180° C., into 1-[2-(2,4-dichlorophenyl)pentyl]-1H-1,2,4-triazole, the symbol R'' in the formulae IIa, IIIa and IVa being hydrogen, methyl or ethyl.

The hydrazones of the formula III and the hydrazines of the formula IV, or the salts thereof, can be isolated in a manner known per se, for example by extraction, distillation, crystallisation or chromatography. An isolation of this kind is however generally not necessary. The process steps 1 and 2 as well as 3 and 4 can hence be carried out as a single-vessel process, a factor which constitutes a further advantage of the process according to the invention.

The intermediates of the formulae III and IV and the salts of compounds of the formula IV with inorganic or organic acids (R=H) are novel, and likewise form subject matter of the present invention. The symbol R herein is preferably H, —CHO, —COR' or —COOR', and R' is methyl or ethyl.

As mentioned at the commencement, the compound of the formula I is a known and valuable fungicide (cp. German Offenlegungsschrift No. 2,735,872).

EXAMPLE 1

1-[2-(2,4-Dichlorophenyl)-pentylidene]-2-acetylhydrazine 100 g of Raney nickel are added to a solution of 228 g (1 mol) of 2-(2,4-dichlorophenyl)-valeronitrile, 74 g (1 mol) of acetylhydrazide and 60 g of acetic acid in 2.3 liters of 95% aqueous ethanol, and the mixture is hydrogenated at room temperature under a normal pressure of hydrogen for 8 hours. Filtration and crystallisation yield 194.8 g (68% of theory) of 1-[2-(2,4-dichlorophenyl)-pentylidene]-2-acetylhydrazine which, after recrystallisation from methanol, has a m.p. of 145°–147° C. and gives the following analytical data: IR spectrum (CHCl$_3$) in cm$^{-1}$: 1672 (CO); $^1$H-NMR spectrum (60 MHz, CDCl$_3$) in ppm: 10.2 (bs, 1H, HN); 7.4–6.7 (m, 4H, 3H—Ar, —CH=N—); 4.2–3.8 (m, 1H, HC(2)); 2.11 (s, 3H, H$_3$C—CO—); 2.2–0.7 (m, 7H, H$_3$C—H$_2$C—H$_2$C—.

mass spectrum: 289/287 (M$^+$ +1).

Elementary analysis for C$_{13}$H$_{16}$Cl$_2$N$_2$O (molecular weight 287.18): Calculated: C, 54.37%; H, 5.62%; N, 9.76%; Cl, 24.69% Found: C, 54.0%; H, 5.7%; N, 9.9%; Cl, 24.7%.

EXAMPLE 2

1-[2-(2,4-Dichlorophenyl)-pentylidene]-2-methoxycarbonylhydrazine 11.0 g of Raney nickel are added to a solution of 22.8 g (0.1 mol) of 2-(2,4-dichlorophenyl)-valeronitrile, 9.0 g (0.1 mol) of hydrazinecarboxylic acid methyl ester and 6.0 g (0.1 mol) of acetic acid in 200 ml of 95% aqueous ethanol, and the mixture is hydrogenated at room temperature under a normal pressure of hydrogen for 6.5 hours. Filtration and crystallisation yield 23.3 g (77% of theory) of the above product, which after recrystallisation from methanol has a melting point of 165°–166° C. and gives the following analytical data: IR spectrum (CHCl$_3$) in cm$^{-1}$: 1750, 1718; $^1$H-NMR spectrum (250 MHz, CDCl$_3$) 8.0 (bs, 1H, HN); 7.41 (d, J=2, 1H, H—Ar); 7.28 (s, 1H, HC=N—); 7.23 (d$_{AB}$xd, J$_{AB}$=8, J=2, 1H, H—Ar); 7.16 (d$_{AB}$, J$_{AB}$=8, 1H, H—Ar); 4.11 (q, J=7, 1H, HC(2)); 3.80 (s, 3H, H$_3$CO—); 2.02–1.68 (m, 2H, H$_2$C(3)); 1.40–1.10 (m, 2H, H$_2$C (4)); 0.88 (t, J=7, 3H, H$_3$C); mass spectrum: 304/302 (M$^+$).

Elementary analysis for C$_{13}$H$_{16}$Cl$_2$N$_2$O$_2$ (molecular weight 303.19): Calculated: C, 51.50%; H, 5.32%; N, 9.24%; O, 10.56%; Cl, 23.39%. Found: C, 51.7%; H, 5.4%; N, 9.3%; O, 10.6%; Cl, 23.5%.

EXAMPLE 3

1-[2-(2,4-Dichlorophenyl)-pentylidene]-2-ethoxycarbonylhydrazine 22.8 g (0.1 mol) of 2-(2,4-dichlorophenyl)-valeronitrile, 10.4 g (0.1 mol) of hydrazinecarboxylic acid ethyl ester and 6.0 g (0.1 mol) of acetic acid are hydrogenated with 11.0 g of Raney nickel in 100 ml of 95% aqueous methanol at room temperature under a normal pressure of hydrogen for 4.5 hours. Filtration and crystallisation yield 22.1 g (70% of theory) of the above product; m.p. 127°–129° C.:

$^1$H-NMR spectrum (60 MHz, CDCl$_3$) in ppm: 7.93 (bs, 1H, HN); 7.4–6.9 (m, 4H, 3 H—Ar, —CH=N—); 4.17 (q, J=7, 2H, —H$_2$C—O); 4.2–3.8 (m, 1H, —CH=N—); 2.2–0.6 (m, 1OH).

Elementary analysis for C$_{14}$H$_{18}$Cl$_2$N$_2$O$_2$ (molecular weight 317.20): Calculated: C, 53.01%; H, 5.72%; N, 8.83%; Cl, 22.35%. Found: C, 53.3%; H, 5.7%; N, 8.9%; Cl, 22.4%.

EXAMPLE 4

1-[2-(2,4-Dichlorophenyl)-pentylidene]-2-formylhydrazine 22.8 g (0.1 mol) of 2-(2,4-dichlorophenyl)-valeronitrile, 6.6 g (0.11 mol) of formylhydrazide and 6.0 g (0.1 mol) of acetic acid are hydrogenated in 100 ml of isopropanol with 11 g of Raney nickel at room temperature under a normal pressure of hydrogen for 24 hours. The reaction mixture is filtered, and the residue after concentration by evaporation is distributed between diethyl ether and water to yield, after column-chromatography, 11.4 g (42% of theory) of the above product.

IR Spectrum (CHCl$_3$) in cm$^{-1}$: 1700 (CO).

$^1$H NMR spectrum (250 MHz, CDCl$_3$) in ppm (J in Hz): 9.7–9.5 (b, 1H, HN); 8.67, 8.63 (2s, 1H, HCO); 7.41 (d, J=2, 1H, H—Ar); 7.26 (s, 1H, HC=N—); 7.24 (d$_{AB}$xd, J$_{AB}$=7, J=2, 1H, H—Ar); 7.15 (d$_{AB}$, J$_{AB}$=7, 1H, H—Ar); 4.08 (m, 1H, HC(2)); 2.05–1.65 (m, 2H, H$_2$C(3)); 1.45–1.1 (m, 2H, H$_2$C(4)); 0.90 (t, J=7, 3H, H$_3$C).

mass spectrum: 274/272 (M+).

EXAMPLE 5

2.0 g of a rhodium/charcoal catalyst (5% by wt. of Rh) are added to a solution of 11.4 g (0.05 mol) of 2-(2,4-dichlorophenyl)-valeronitrile, 3.7 g (0.05 mol) of acetylhydrazide and 3.0 g (0.05 mol) of acetic acid in 140 ml of methanol, and the mixture is hydrogenated at room temperature under a normal pressure of hydrogen for 8 hours. 1-[2-(2,4-Dichlorophenyl)-pentylidene]-2-acetylhydrazine is thus obtained in a yield of 49% of theory (determined by gas chromatography).

EXAMPLE 6

1-[2-(2,4-Dichlorophenyl)-pentyl]-2-acetylhydrazine (a) 2.5 g of Raney nickel are added to a solution of 14.3 g (0.05 mol) of 1-[2-(2,4-dichlorophenyl)-pentylidene]-2-acetylhydrazine in 150 ml of isopropanol, and the mixture is hydrogenated at 80° C. under 100 bar of hydrogen pressure for 16 hours. Filtration and chromatography of the residue after concentration by evaporation yield 10.9 g (76% of theory) of the above product.

$^1$H-NMR spectrum (60 MHz, CDCl$_3$) in ppm: in the presence of a trace of trifluoroacetic acid: 8.32 (bs, 2H, 2HN); 7.4–7.0 (m, 3H, 3 H—Ar); 3.7–2.9 (m, 3H, H$_2$C(1), HC(2)); 1.90 (s, 3H, H$_3$C); 2.0–0.6 (m, 7H).

(b) 1.0 g of a platinum/charcoal catalyst (5% by wt. of Pt) is added to a solution of 49.0 g (0.17 mol) of 1-[2-(2,4-dichlorophenyl)-pentylidene]-2-acetylhydrazine in 170 ml of abs. ethanol; and the mixture is then hydrogenated at 50° C. under 50 bar of hydrogen pressure for 5 hours. The yield after filtering off the catalyst and evaporating off the ethanol is 49.0 g of an oily residue, which, according to gas-chromatographic analysis, consists to the extent of 95% by weight of 1-[2-(2,4-dichlorophenyl)-pentyl]-2-acrylhydrazine; yield: 95% of theory.

EXAMPLE 7

1-[2-(2,4-Dichlorophenyl)-pentyl]-2-methoxycarbonylhydrazine 1.2 g of a platinum/charcoal catalyst (5% by weight of Pt) are added to a solution of 12.0 g (0.04 mol) of 1-[2-(2,4-dichlorophenyl)-pentylidene]-2-methoxycarbonylhydrazine in 80 ml of acetic acid, and the mixture is hydrogenated at 40° C. under a hydrogen pressure of 50 bar for 2 hours. Filtration of the reaction mixture and column-chromatography of the residue after evaporation yield 9.4 g (78% of theory) of the above product:

$^1$H-NMR spectrum (250 MHz, CDCL$_3$) in ppm: in the presence of D$_2$O: 7.39 (d, J=2, 1H, H—Ar); 7.27 (s, 1H, HC=N—); 7.26 (d$_{AB}$xd, J$_{AB}$=8, J=2, 1H, H—Ar); (d$_{AB}$, J$_{AB}$=8, 1H, H—Ar); 4.80 (bs, DHO); 3.71 (s, 3H, H$_3$CO—); 3.50–3.36 (m, 1H, HC(2)); 3.20–2.95 (m, 2H, H$_2$C (1)); 1.55–1.44 (m, 2H, H$_2$C(3)); 1.35–1.05 (m, 2H, H$_2$C(4)); 0.85 (t, J=7, 3H, H$_3$C).

EXAMPLES 8-11

By a procedure analogous to that of Example 6, 1-[2-(2,4-dichlorophenyl)-pentylidene]-2-acetylhydrazine is hydrogenated, under the reaction conditions given in the following Table, to 1-[2-(2,4-dichlorophenyl)-pentyl]-2-acetylhydrazine.

TABLE

| Ex. No. | Catalyst | H$_2$ pressure bar | Temp. °C. | Solvent** | Yield % of theory* |
|---|---|---|---|---|---|
| 8 | Pt/C (5% by wt. of Pt) | 50 | 100 | methanol/ethyl acetate | 61 |
| 9 | Ra/Ni | 50 | 100 | methanol/ethyl acetate | 89 |
| 10 | Ru/C (10% by wt. of Ru) | 50 | 80 | methanol/ethyl acetate | 27 |
| 11 | Rh/C (5% by wt. of Rh) | 50 | 100 | methanol/ethyl acetate | 37 |

*determined by gas-chromatographic analysis
**in the volume ratio of 1:1

EXAMPLE 12

1-[2-(2,4-dichlorophenyl)-pentyl]-1H-1,2,4-triazole 5.2 g (0.018 mol) of 1-[2-(2,4-dichlorophenyl)pentyl]-2-acetyl-hydrazine are heated in a mixture of 10 ml of ethanol, 10 ml of water and 10 ml of concentrated hydrochloric acid at 90° C. for 1 hour. The subsequently cooled reaction mixture is distributed between diethyl ether and 2 N sodium hydroxide solution, and the ether phase is dried and concentrated by evaporation. The residue is slowly heated in 50 ml of formamide to 180° C., and this temperature is held for 2 hours. The cooled reaction mixture is then distributed between diethyl ether and water. Chromatographing the residue obtained by evaporation yields 2.8 g (55% of theory) of the above product: $^1$H-NMR spectrum (60 MHz, CDCl$_3$) identical to the NMR spectrum of 1-[2-(2,4-dichlorophenyl)-pentyl]-1H-1,2,4-triazole, which has been produced by replacement of the methanesulfonate of 2-(2,4-dichlorophenyl)pentan-1-ol by the sodium salt of 1,2,4-triazole; in ppm: 7.80 (s, 1H, H-triazole); 7.67 (s, 1H, H-triazole); 7.4–6.9 (m, 3H, H$_3$Ar); 4.37, 4.27 (2s, 2H, H$_2$C(1)); 4.1–3.5 (m, 1H,HC(2)); 2.0–0.6 (m, 7H).

EXAMPLE 13

5.1 g (0.017 mol) of 1-[2-(2,4-dichlorophenyl)pentyl]-2acetylhydrazine in 10 ml of ethanol and 10 ml of concentrated hydrochloric acid are stirred at 50° C. overnight. The reaction mixture is then distributed between diethyl ether and 2 N sodium hydroxide solution; and the residue after concentration by evaporation is refluxed in 50 ml of absolute ethanol with 5.75 g (0.035 mol) of [3-(dimethylamino)-2-aza-prop-2-en-1-ylidene]-dimethylammonium chloride for 3.5 hours. The reaction solution is then concentrated by evaporation; 50 ml of formamide are added, and the mixture is heated at 170° C. for 1.5 hours. The reaction mixture, to which water has been added, is extracted with diethyl ether, and the residue obtained after concentration by evaporation is chromatographed to yield 4.2 g (84% of theory) of 1-[2-(2,4-dichlorophenyl)-pentyl]-1H-1,2,4-triazole.

EXAMPLE 14

1-[2-(2,4-dichlorophenyl)-pentyl]-1,2-diformylhydrazine 5.0 g (0.017 mol) of 1-[2-(2,4-dichlorophenyl)-pentyl-2-acetylhydrazine in 20 ml of 85% aqueous formic acid are heated for 18 hours at 100° C. Column-chromatography of the residue obtained after concentration by evaporation yields pure 1-[2-(2,4-dichlorophenyl)-pentyl]-1,2-diformylhydrazine:

IR spectrum (CHCl$_3$) in cm$^{-1}$: 1720, 1685 (CO).

$^1$H-NMR spectrum (100 MHz, CDCl$_3$): δ in ppm; in the presence of D$_2$O: 8.14, 8.13, 8.08, 7.93, 7.90, 7.73 (6s, 2H, 2 CHO); 7.5–6.9 (m, 3H, 3H—Ar); 4.66 (s, 1H, HDO); 4.0–3.2 (m, 3H, H$_2$C(1), HC(2)); 1.9–1.45 (m, 2H, H$_2$C (3)); 1.45–1.0 (m, 2H, H$_2$C (4)); 1.0–0.7 (m, 3H, H$_3$C(5)).

EXAMPLE 15

1-[2-(2,4-dichlorophenyl)-pentyl]-1H-1,2,4-triazole 6.2 g of the 1-[2-(2,4-dichlorophenyl)-pentyl-1,2-diformylhydrazine obtained according to Example 14 are heated, without purification, in 50 ml of formamide at 170° C. for 6 hours. Chromatography of the product obtained yields 1-[2-(2,4-dichlorophenyl)-pentyl]-1H-1,2,4-triazole, the $^1$H-NMR spectrum of which agrees with the $^1$H-NMR spectrum of the same compound described in Example 12.

Example 16

1-[2-(2,4-dichlorophenyl)-pentyl]-1H-1,2,4-triazole 57.8 g (0.2 mol) of 1-[2-(2,4-dichlorophenyl)-pentyl]-2-acetylhydrazine are refluxed with 216.5 g of formic acid (85%: 4.0 mols) for 20 hours. Volatile fractions (formic acid, acetic acid and water) are subsequently distilled off at 95° C./100 mbar. To the residue are added 38.5 g (0.61 mol) of ammonium formiate and 220 g (4.9 mols) of formamide, and the mixture is heated at 160° C. for 8 hours. The reaction mixture is then cooled to 20° C. and toluene is added. After separation of the lower layer, consisting of formamide and water, the toluene layer is washed with 100 ml of water and subsequently concentrated by evaporation. There are obtained 52.9 g of a slowly crystallising oil which, according to gas-chromatographic analysis, consists to the extent of 90.1% by weight of 1-[2-(2,4-dichlorophenyl)-pentyl]-1H-1,2,4-triazole. This corresponds to a yield of 83.9% of theory, relative to the employed 1-[2-(2,4-dichlorophenyl)-pentyl]-2-acetyl-hydrazine.

What is claimed is:

1. A process for producing 1-[2-(2,4-dichlorophenyl)-pentyl]-1H-1,2,4-triazole of the formula

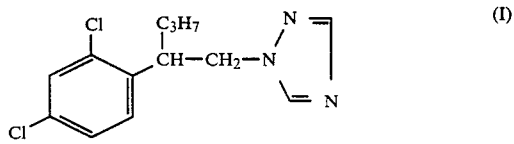

which process comprises reacting 2-(2,4-dichlorophenyl)-valeronitrile, in the presence of hydrogen, an acid and a hydrogenation catalyst, with a compound of the formula II $$H_2N-NH-R \quad (II)$$

to give a compound of the formula III

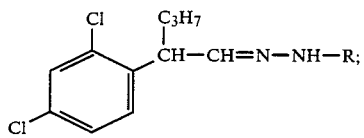

hydrogenating the compound of the formula III catalytically to a compound of the formula IV

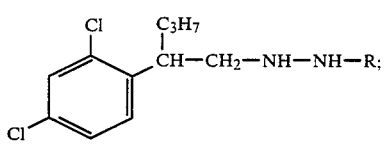

and subsequently either (a) hydrolysing a compound of the formula IV wherein R is not hydrogen, and converting the compound of the formula IV wherein R=H, or a salt thereof with an inorganic or organic acid, with formamide, and/or with (3-(dimethylamino)-2-azaprop-2-en-1-ylidene)-dimethylammonium chloride, into the compound of the formula I or (b) converting a compound of the formula IV wherein R is —COR', with aqueous formic acid, into an N,N'-bisformyl derivative, and reacting this with formamide, optionally in the presence of NH$_3$ or of a substance releasing NH$_3$, into a compound of the formula I; where R is —CHO, —COR' or —COOR', and R' is methyl or ethyl.

2. A process according to claim 1, wherein there is used a compound of the formula II wherein R is —COR", and R" is hydrogen, methyl or ethyl.

3. A process according to claim 1, wherein the reaction of 2-(2,4-dichlorophenyl)-valeronitrile with the hydrazine of the formula II is performed in an organic or aqueous-organic medium.

4. A process according to claim 1, wherein the reaction of 2-(2,4-dichlorophenyl)-valeronitrile with the hydrazine of the formula II is performed in a C$_1$–C$_4$-alkanol, or in a mixture thereof with water.

5. A process according to claim 1, wherein Raney nickel or rhodium on a carrier is used as a hydrogenation catalyst for the reaction of 2-(2,4-dichlorophenyl)-valeronitrile with the hydrazine of the formula II.

6. A process according to claim 1, wherein the reaction of 2-(2,4-dichlorophenyl)-valeronitrile with the hydrazine of the formula II is performed in the presence of an aliphatic monocarboxylic acid having 1–4 C atoms.

7. A process according to claim 1, wherein the hydrogenation of a hydrazone of the formula III to a hydrazine of the formula IV is performed in the presence of an organic solvent selected from the group consisting of acetic acid, methanol, ethanol, isopropanol, sec-butanol, tert-butanol, or mixtures of any of said alcohols with ethyl acetate.

8. A process according to claim 1, wherein the catalyst used for the hydrogenation of the hydrazone of the formula III to the hydrazine of the formula IV is a Raney nickel, rhodium or platinum catalyst.

9. A process according to claim 1, which comprises reacting 2-(2,4-dichlorophenyl)-valeronitrile, in the presence of acetic acid and a hydrogenation catalyst, with an acylhydrazine of the formula IIa $$H_2N-NH-COR''\qquad(IIa)$$

to a 1-[2-(2,4-dichlorophenyl)-pentylidene]-2-acylhydrazine of the formula IIIa

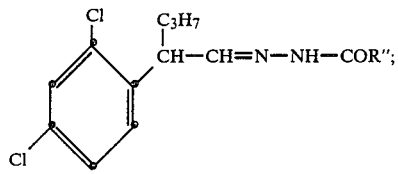
(IIIa)

hydrogenating this to 1-[2-(2,4-dichlorophenyl)-pentyl]-2-acylhydrazine of the formula IVa

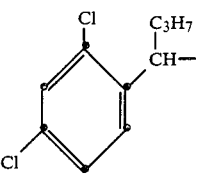
(IVa)

and converting this, by reaction with formic acid, firstly into 1-[2-(2,4-dichlorophenyl)-pentyl]1,2-diformylhydrazine, and this, by further reaction with formamide at 120°–180° C., into 1-[2-(2,4-dichlorophenyl)-pentyl]-1H-1,2,4-triazole; the symbol R" in the formulae IIa, IIIa and IVa being hydrogen, methyl or ethyl.

* * * * *